(12) United States Patent
Kawamoto et al.

(10) Patent No.: US 10,524,416 B2
(45) Date of Patent: Jan. 7, 2020

(54) WORK VEHICLE

(71) Applicant: Kubota Corporation, Osaka-shi (JP)

(72) Inventors: Kazuyoshi Kawamoto, Sakai (JP); Shunsuke Fujii, Sakai (JP)

(73) Assignee: Kubota Corporation, Osaka (JP)

( * ) Notice: Subject to any disclaimer, the term of this patent is extended or adjusted under 35 U.S.C. 154(b) by 57 days.

(21) Appl. No.: 15/825,487

(22) Filed: Nov. 29, 2017

(65) Prior Publication Data

US 2018/0177123 A1 Jun. 28, 2018

(30) Foreign Application Priority Data

Dec. 27, 2016 (JP) .................. 2016-253471

(51) Int. Cl.
| | |
|---|---|
| A01D 34/68 | (2006.01) |
| A01D 34/78 | (2006.01) |
| A01D 34/00 | (2006.01) |
| A01C 7/10 | (2006.01) |
| G06K 9/20 | (2006.01) |
| G06T 7/00 | (2017.01) |
| G06K 9/00 | (2006.01) |
| A01D 43/14 | (2006.01) |
| A01C 21/00 | (2006.01) |
| G01N 21/84 | (2006.01) |

(52) U.S. Cl.
CPC .......... A01D 34/6806 (2013.01); A01C 7/102 (2013.01); A01C 21/005 (2013.01); A01D 34/008 (2013.01); A01D 34/78 (2013.01); A01D 43/14 (2013.01); G06K 9/00657 (2013.01); G06K 9/00664 (2013.01); G06K 9/2009 (2013.01); G06T 7/001 (2013.01); G01N 2021/8466 (2013.01); G06T 2207/30188 (2013.01)

(58) Field of Classification Search
CPC ......... A01C 7/102; A01C 7/00; A01C 21/005; A01D 34/008
See application file for complete search history.

(56) References Cited

FOREIGN PATENT DOCUMENTS

| | | | |
|---|---|---|---|
| JP | 2000245215 A | | 9/2000 |
| JP | 2003250318 A | | 9/2003 |
| JP | 2012198688 A | * | 10/2012 |
| JP | 2014042490 A | | 3/2014 |
| JP | 201523819 A | | 2/2015 |
| JP | 2016202061 A | | 12/2016 |
| KR | 101406210 B1 | * | 6/2014 |

OTHER PUBLICATIONS

KR101406210, Machine Translation (Year: 2014).*
JP-2012198688-A—Machine Translation (Year: 2012).*
"The lawn in the vestibular, further chase", 2009, https://yaplog.jp/unterrichten/archive/329 (downloaded from the internet Oct. 16, 2019).

* cited by examiner

Primary Examiner — Abby Y Lin
Assistant Examiner — Renee LaRose
(74) Attorney, Agent, or Firm — The Webb Law Firm

(57) ABSTRACT

A work vehicle includes an imaging device for imaging a plant growing in a field and a control device for controlling a sowing device. The control device includes a growth state determination section for determining a growth state of the plant in the field based on result of imaging by the imaging device and a sowing instruction section for instructing the sowing device to carry out a seed sowing operation based on result of determination of the growth state determination section.

9 Claims, 3 Drawing Sheets

WORK VEHICLE

CROSS-REFERENCE TO RELATED APPLICATION

This application claims priority to Japanese Patent Application No. 2016-253471 filed Dec. 27, 2016, the disclosure of which is hereby incorporated in its entirety by reference.

BACKGROUND OF THE INVENTION

1. Field of the Invention

This invention relates to a work vehicle including an imaging device for imaging a plant growing in a field.

2. Description of the Related Art

A work vehicle disclosed in JP 2014-042490 A includes a front camera for imaging a turf surface area present in an advancing direction. A location where turf is shaved and exposed (called a "divot" in JP 2014-042490 A) is detected from the image and a sand filling work for the divot is carried out. However, JP 2014-042490 A discloses only that a sand filling work for the divot is carried out based on result of imaging by the imaging device. There remains room for improvement for efficiently carrying out field management.

SUMMARY OF THE INVENTION

Then, there is proposed a work vehicle as under:
A work vehicle comprising:
an imaging device for imaging a plant growing in a field;
a sowing device for sowing seeds in the field; and
a control device for controlling the sowing device, the control device including:
  a growth state determination section for determining a growth state of the plant in the field based on result of imaging by the imaging device; and
  a sowing instruction section for instructing the sowing device to carry out a seed sowing operation based on result of determination of the growth state determination section.

With the above arrangement, while an imaging operation is being carried out by the imaging device, seeds can be sown at a location where the growth state of the plant is poor, whereby field management can be carried out in an efficient manner.

According to one preferred embodiment, the work vehicle further comprises: a vehicle speed sensor for detecting a vehicle speed of the work vehicle;
wherein:
the imaging device is disposed at a front portion of a vehicle body;
the sowing device is disposed at a rear portion of the vehicle body;
the control device includes an expected passage time calculation section for calculating an expected passage time when the sowing device is expected to pass over the plant imaged by the imaging device; and
the sowing instruction section instructs the sowing device to carry out the seed sowing operation when the expected passage time calculated by the expected passage time calculation section has lapsed.

With the above arrangement, a slight time lag occurs until the sowing device passes over the plant imaged by the imaging device. Then, as the sowing instruction section instructs the sowing device to carry out the seed sowing operation when the expected passage time calculated by the expected passage time calculation section has lapsed, seeds can be sown in the field in accordance with the timing of locating of the sowing device on the plant imaged by the imaging device.

According to another preferred embodiment, the control device includes a growth density calculation section for calculating growth density of the plant in the field based on the result of imaging of the imaging device; and
the growth state determination section determines the growth state of the plant in the field based on result of calculation by the growth density calculation section.

If the growth density of the plant in the field is high, it can be assumed that the growth state of the plant in the field is good. If the growth density of the plant in the field is low, it can be assumed that the growth state of the plant in the field is poor. With the above arrangement, the growth state of the plant in the field can be determined in an accurate manner.

According to still another preferred embodiment, the control device further includes:
  a location information acquisition section for acquiring location information of the vehicle body; and
  a correlation section for correlating the location information acquired by the location information acquisition section, with the result of calculation by the growth density calculation section.

With the above arrangement, by correlating the location information acquired by the location information acquisition section with the result of calculation by the growth density calculation section, it is possible to obtain information (e.g. a field map) useful for efficiently carrying out the field management.

According to still yet another preferred embodiment, the sowing device includes:
  a storage section for storing seeds; and
  an opening/closing member for opening/closing a feed opening for feeding the seeds in the storage section to the field; and
  wherein the sowing instruction section instructs the sowing device to carry out the sowing operation in such a manner that the lower is the growth density of the plant in the field, the greater becomes the opening degree of the opening/closing member.

With the above arrangement, the lower the growth density of the plant in the field, the greater the amount of seeds to be sown in the field. Thus, the sowing operation can be carried out in an efficient manner.

According to one preferred embodiment, the work vehicle comprises a riding type lawn mower.

With the above arrangement, by carrying out a lawn mowing operation and a sowing operation as a series of operations, the work can be carried out in an efficient manner.

In the case of a riding type lawn mower, if the sowing device is disposed on more rear side than a mower device for mowing lawn in a field, seeds will be sown in the field by the sowing device after lawn in the field is mowed by the mowing device. With this, the seeds can reach the ground surface more easily than a case of sowing the seeds in the field where lawn has grown fully.

Further, when the imaging device images an area before lawn has been mowed by the mowing device, this area prior to mowing by the mowing device will show the present growth state of the lawn in the field clearly, so that the growth state of the lawn in the field can be determined accurately.

Further and other features and advantageous effects achieved thereby will become apparent upon reading the following explanation with reference to the accompanying drawings.

DETAILED DESCRIPTION OF PREFERRED EMBODIMENTS

An exemplary embodiment of a work vehicle according to the present invention will be described next with reference to the drawings.

General Configuration of Riding Type Lawn Mower

Figure 1:
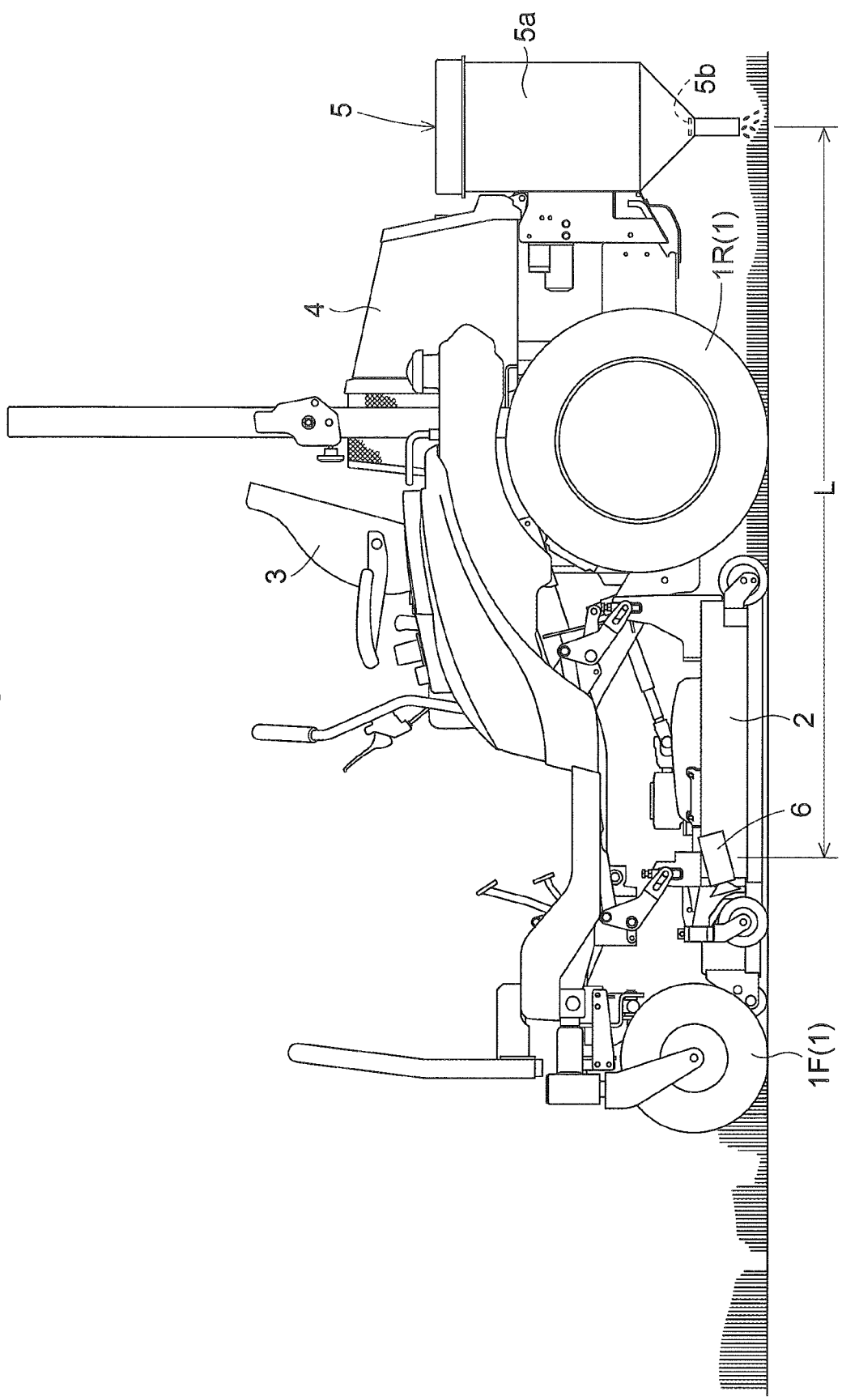
FIG. 1 is a left side view showing a riding type lawn mower as an example of a work vehicle according to one embodiment of the invention.

FIG. 1 shows a riding type lawn mower as an example of a "work vehicle" directed to the present invention. In the instant embodiment, lawn is assumed as a "plant" related to the invention. The riding type lawn mower includes a traveling device 1. The traveling device 1 includes a pair of right and left front wheels 1F and a pair of right and left rear wheels 1R. A mower deck 2 (corresponding to a "mowing device") is provided between the front wheels 1F and the rear wheels 1R for mowing lawn in a field. A driver's seat 3 is provided at a center portion of the vehicle body. A hood 4 is provided rearwardly of the driver's seat 3 for accommodating an engine (not shown), etc.

A sowing device 5 is provided rearwardly of the hood 4 for sowing seeds (lawn seeds) in the field. The sowing device 5 is disposed at a rear portion of the vehicle body. Namely, the sowing device 5 is on more rear side than the mower deck 2. The sowing device 5 includes a storage section 5a for storing seeds and a shutter 5b (corresponding to an "opening/closing member") for opening/closing a feed opening (not shown) for feeding seeds inside the storage section 5a to the field.

A camera 6 (corresponding to an "imaging device") is mounted at a front portion of the mower deck 2 for imaging lawn growing in the field. The camera 6 is disposed at a front portion of the vehicle body. The camera 6 captures images of an area before lawn is mowed by the mower deck 2.

Control Device

Figure 2:
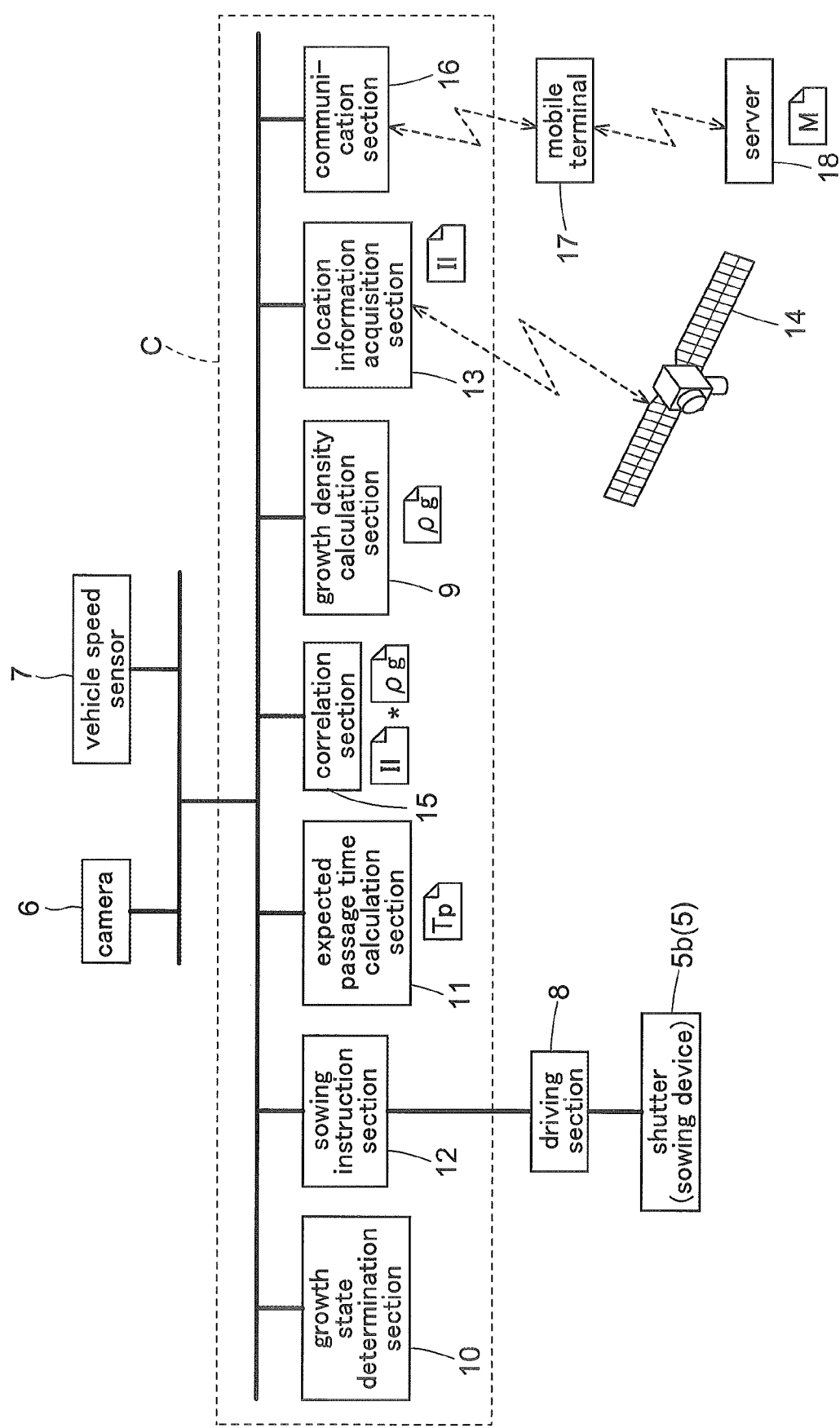
FIG. 2 is a control block diagram of the embodiment.

FIG. 2 shows a control device C (an electric control unit or an ECU in the instant embodiment) mounted on the riding type lawn mower. The camera 6 and a vehicle speed sensor 7 for detecting a vehicle speed are connected to the input side of the control device C. A driving section 8 is connected to the output side of the control device C for driving opening/closing of the shutter 5b. The control device C includes: a growth density calculation section 9, a growth state determination section 10, an expected passage time calculation section 11, a sowing instruction section 12, a location information acquisition section 13, a correlation section 15 and a communication section 16.

The growth density calculation section 9 calculates a growth density ($\rho g$) of the lawn in the field, based on the result of imaging (image) of the camera 6. The growth state determination section 10 determines a growth state of lawn in the field, based on the result of calculation (growth density $\rho g$) of the growth density calculation section 9. Specifically, the growth state determination section 10 determines that the growth state of lawn in the field is "not good" if the growth density ($\rho g$) is less than a reference growth density ($\rho s$) (i.e. $\rho g < \rho s$); and determines that the growth state of lawn in the field is "good" if the growth density ($\rho g$) is equal to or higher the reference growth density ($\rho s$) (i.e. $\rho g >= \rho s$).

The expected passage time calculation section 11 calculates an expected passage time (Tp) when the sowing device 5 passes over the lawn imaged by the camera 6. In this case, if a distance (L) (see FIG. 1) between the camera 6 and the imaging device 5 in the vehicle body front-rear direction is known, the expected passage time (Tp) can be calculated by dividing the distance (L) by the vehicle speed (i.e. L/vehicle speed).

The sowing instruction section 12 instructs the sowing device 5 to carry out a sowing operation, based on the result of determination by the growth state determination section 10. In this, the sowing instruction section 13 instructs the sowing device 5 to carry out the sowing operation, such that the lower is the growth density ($\mu g$), the greater becomes the opening degree of the shutter 5b. More particularly, the sowing instruction section 12 switches the opening degree of the shutter 5b in three stages (closed stage, small opening stage and large opening stage) in accordance with the growth density ($\mu g$). Also, the sowing instruction section 12 instructs the sowing device 5 to carry out the sowing operation upon lapse of the expected passage time (Tp), such that the sowing device 5 sows seeds in the field in accordance with the timing at which the sowing device 5 is located on the lawn imaged by the camera 6.

The location information acquisition section 13 acquires location information (I1) of the vehicle body by receiving radio wave from a global positioning system (GPS) 14. The correlation section 15 correlates the vehicle body location information (I1) acquired by the location information acquisition section 13 with the growth density ($\rho g$).

The communication section 16 effects communication with a server 18 via a mobile terminal 17 (e.g. a smartphone, a tablet, etc.) carried by the operator (or not via the mobile terminal 17). The information correlated by the correlation section 15 (position information I1 multiplied by growth density $\rho g$) (i.e. I1*$\rho g$)) is transmitted from the communication section 16 to the server 18. In the server 18, a field map M related to the position information (I1) and the growth density ($\rho g$) is produced. As the communication section 16 receives the field map P from the server 18, the field map M can be utilized for field management.

Control Flow

Figure 3:
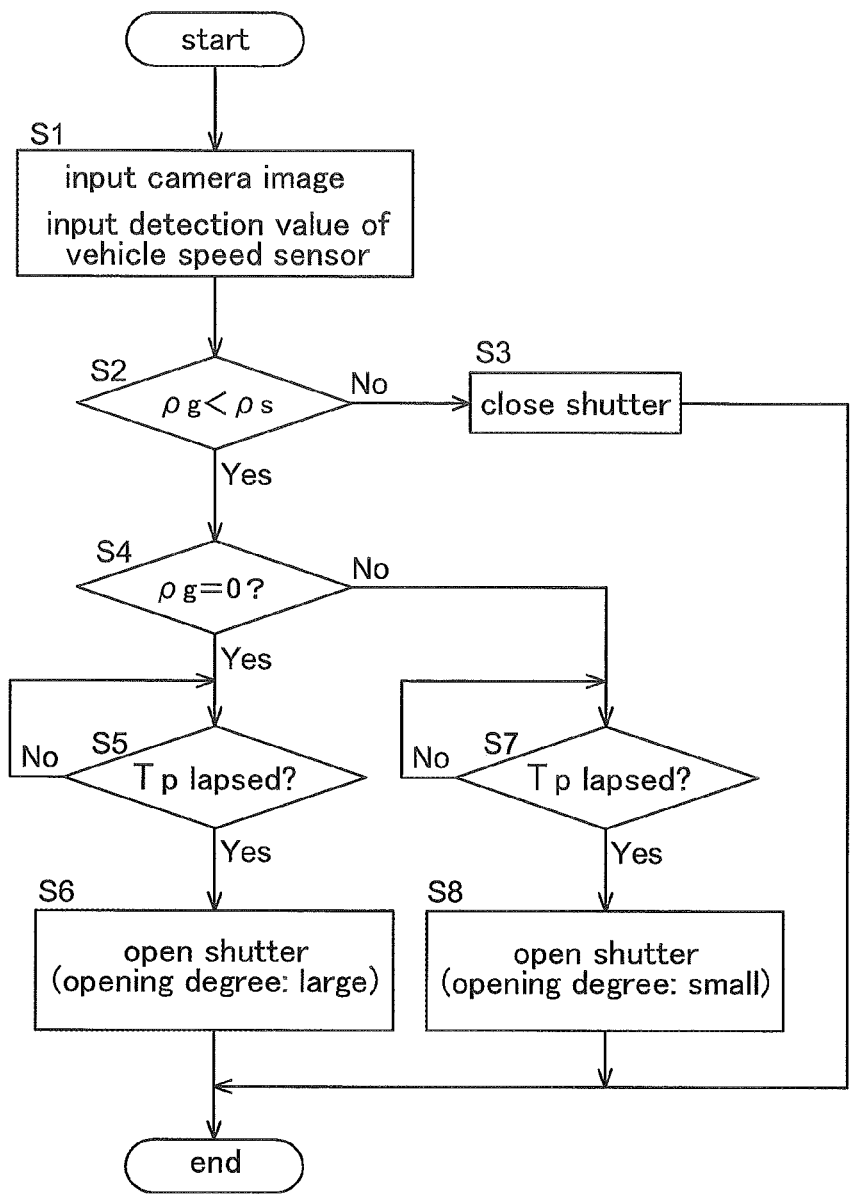
FIG. 3 is a control flowchart of the embodiment.

As shown in FIG. 3, images of the camera 6 and detection values of the vehicle speed sensor 7 are inputted continuously to the control device C (step S1).

At step S2, the growth state determination section 10 determines that the growth state of lawn in the field is "good" if the growth density ($\rho g$) is equal to or higher than the reference growth density ($\rho s$) (i.e. $\rho g >= \rho s$) (step S2: No). In this case, the shutter 5b will be maintained under a closed state (step S3).

On the other hand, at step S2, the growth state determination section 10 determines that the growth state of lawn in the field is "not good" if the growth density ($\rho g$) is less than the reference growth density $\rho s$ (i.e. $\rho g<\rho s$) (step S2: Yes).

Then, at step S4, if the growth density ($\rho g$) is 0 (zero) ($\rho g=0$) (step S4: Yes), the sowing instruction section 12 instructs the sowing device 5 to carry out a sowing operation when an expected passage time (Tp) has lapsed (step S5: Yes). With this, the shutter 5b is switched to the opened state (the large opening stage) by the driving section 8 (step S6).

On the other hand, at step S4, if the growth density ($\rho g$) is not 0 (zero) ($0<\rho g<\rho s$) (step S4: No), the sowing instruction section 12 instructs the sowing device 5 to carry out a sowing operation when an expected passage time (Tp) has lapsed (step S7: Yes). With this, the shutter 5b is switched to the opened state (the small opening stage) by the driving section 8 (step S8).

Other Embodiments (1) In the foregoing embodiment, the growth state determination section 10 determines a growth state of lawn in the field, based on the growth density ($\rho g$). Instead thereof, the growth state determination section 10 can determine the growth state of the lawn in the field, based on a factor other than growth density ($\rho g$) (e.g. color of the lawn, etc.).

(2) In the foregoing embodiment, the sowing instruction section 12 switches the opening degree of the shutter 5b in three stages (closed stage, small opening stage and large opening stage) in accordance with the growth density ($\rho g$). Instead thereof, the sowing instruction section 12 can switch the opening degree of the shutter 5b in four or more stages in accordance with the growth density ($\rho g$). Or, the sowing instruction section 12 can switch the opening degree of the shutter 5b in two stages (closed stage and opened stage).

(3) In the foregoing embodiment, lawn is assumed as a "plant" related to the invention. However, the "plant" related to the invention is not limited to lawn.

(4) The present invention is applicable not only to the riding type lawn mower as one illustrated in the foregoing embodiment, but also to a work vehicle not having a mowing device.

What is claimed is:
1. A work vehicle comprising:
an imaging device for imaging a plant growing in a field;
a sowing device for sowing seeds in the field; and
a control device for controlling the sowing device, the control device including:
a growth state determination section for determining a growth state of the plant in the field based on result of imaging by the imaging device; and
a sowing instruction section for instructing the sowing device to carry out a seed sowing operation based on result of determination of the growth state determination section,
wherein the work vehicle comprises a riding type lawn mower.
2. The work vehicle according to claim 1, further comprising:
a vehicle speed sensor for detecting a vehicle speed of the work vehicle;
wherein:
the imaging device is disposed at a front portion of a vehicle body;
the sowing device is disposed at a rear portion of the vehicle body;
the control device includes an expected passage time calculation section for calculating an expected passage time when the sowing device is expected to pass over the plant imaged by the imaging device; and
the sowing instruction section instructs the sowing device to carry out the seed sowing operation when the expected passage time calculated by the expected passage time calculation section has lapsed.
3. The work vehicle according to claim 1, wherein:
the control device includes a growth density calculation section for calculating growth density of the plant in the field based on the result of imaging of the imaging device; and
the growth state determination section determines the growth state of the plant in the field based on result of calculation by the growth density calculation section.
4. The work vehicle according to claim 3, wherein:
the control device further includes:
a location information acquisition section for acquiring location information of the vehicle body; and
a correlation section for correlating the location information acquired by the location information acquisition section, with the result of calculation by the growth density calculation section.
5. The work vehicle according to claim 3, wherein:
the sowing device includes:
a storage section for storing seeds; and
an opening/closing member for opening/closing a feed opening for feeding the seeds in the storage section to the field; and
wherein the sowing instruction section instructs the sowing device to carry out the sowing operation in such a manner that the lower is the growth density of the plant in the field, the greater becomes the opening degree of the opening/closing member.
6. The work vehicle according to claim 1, further comprising:
a mower device for mowing lawn in the field, the sowing device being disposed on more rear side than the mower device.
7. The work vehicle according to claim 6, wherein the imaging device images an area before lawn has been mowed by the mower device.
8. A work vehicle comprising:
an imaging device for imaging a plant growing in a field;
a vehicle speed sensor for detecting a vehicle speed of the work vehicle;
a sowing device for sowing seeds in the field; and
a control device for controlling the sowing device, the control device including:
a growth state determination section for determining a growth state of the plant in the field based on result of imaging by the imaging device; and
a sowing instruction section for instructing the sowing device to carry out a seed sowing operation based on result of determination of the growth state determination section,
wherein:
the imaging device is disposed at a front portion of a vehicle body;
the sowing device is disposed at a rear portion of the vehicle body;
the control device includes an expected passage time calculation section for calculating an expected passage time when the sowing device is expected to pass over the plant imaged by the imaging device; and the sowing instruction section instructs the sowing device to carry out the seed sowing operation when the expected passage time calculated by the expected passage time calculation section has lapsed.

9. A work vehicle comprising:
an imaging device for imaging a plant growing in a field;
a sowing device for sowing seeds in the field; and
a control device for controlling the sowing device, the control device including:
   a growth state determination section for determining a growth state of the plant in the field based on result of imaging by the imaging device; and
   a sowing instruction section for instructing the sowing device to carry out a seed sowing operation based on result of determination of the growth state determination section,
wherein:
the control device includes a growth density calculation section for calculating growth density of the plant in the field based on the result of imaging of the imaging device; and
the growth state determination section determines the growth state of the plant in the field based on result of calculation by the growth density calculation section.

* * * * *